United States Patent [19]

Martin et al.

[11] 4,255,351
[45] Mar. 10, 1981

[54] SULFONIC ACID ESTERS OF 2,2,2-TRICHLOROETHYLHYDROXYCYCLOBUTANONES

[75] Inventors: Pierre Martin, Rheinfelden, Switzerland; Hans Greuter, Cos Cob, Conn.; Daniel Bellus, Riehen, Switzerland

[73] Assignee: Ciba-Geigy Corporation, Ardsley, N.Y.

[21] Appl. No.: 17,872

[22] Filed: Mar. 5, 1979

[30] Foreign Application Priority Data

Mar. 14, 1978 [CH] Switzerland .................. 27587/78

[51] Int. Cl.³ .................................................. C07C 143/68
[52] U.S. Cl. ............................. 260/456 R; 260/456 P; 260/347.2; 260/347.5; 568/348; 568/374; 568/381; 562/506; 560/124; 549/66; 549/79
[58] Field of Search ...................... 260/456 R, 456 P

[56] References Cited

U.S. PATENT DOCUMENTS

| | | | |
|---|---|---|---|
| 3,309,403 | 3/1967 | Mador | 260/544 |
| 3,361,811 | 1/1968 | Ihrman et al. | 260/544 |
| 3,423,456 | 1/1969 | Mador et al. | 260/544 |
| 3,728,372 | 4/1973 | Siddal | 260/456 R |
| 4,128,584 | 12/1978 | Martel et al. | 260/456 R |

*Primary Examiner*—Nicky Chan
*Attorney, Agent, or Firm*—Frederick H. Rabin

[57] ABSTRACT

Compounds of the formulae Ia, Ib, IIa and IIb

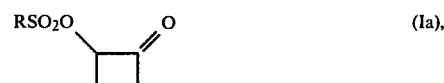 (Ia),

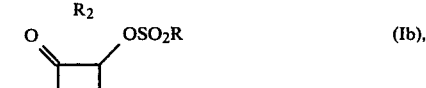 (Ib),

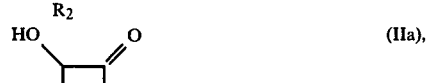 (IIa),

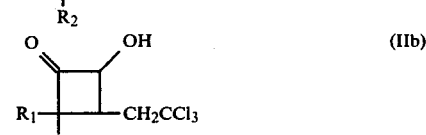 (IIb)

are described, wherein R represents alkyl, haloalkyl, benzyl, naphthyl or substituted or unsubstituted phenyl and one of $R_1$ and $R_2$ represents methyl and the other represents hydrogen or methyl, or $R_1$ and $R_2$ together represent alkylene of 2 or 3 carbon atoms. The compound of the formulae Ia, Ib, IIa and IIb are valuable intermediates for the manufacture of pyrethroid pesticides or precursors thereof.

2 Claims, No Drawings

SULFONIC ACID ESTERS OF 2,2,2-TRICHLOROETHYLHYDROXYCYCLOBUTANONES

The present invention relates to novel sulfonic acid esters of 2,2,2-trichloroethylhydroxycyclobutanones and a process for their manufacture. These compounds are valuable intermediates for the production of pyrethroid pesticides.

It is known that cyclobutanones with suitable leaving groups in the α-position, such as halogen atoms or sulfonic acid ester groups, are converted into cyclopropanecarboxylic acid derivatives in the presence of bases, for example alkali metal hydroxides or alkali metal alcoholates, with ring contraction (Favorski reaction). The use of this process, which is technically easy to carry out, for the production of pyrethroids which are derived from 2-(2',2'-dichlorovinyl)-cyclopropanecarboxylic acid, has up to now been hindered because of the difficulty of obtaining corresponding cyclobutanones for the manufacture of such cyclopropanecarboxylic acid derivatives. Accordingly, it is the object of the present invention to provide such cyclobutanone derivatives starting from easily obtainable starting materials.

The invention is therefore concerned with the provision of novel sulfonic acid esters of 2,2,2trichloroethylhydroxycyclobutanones of the formula Ia or Ib

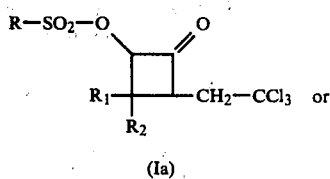

(Ia)

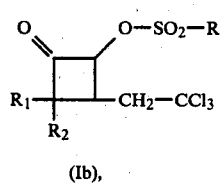

(Ib), wherein R represents alkyl, haloalkyl, benzyl, naphthyl or substituted or unsubstituted phenyl, one of $R_1$ and $R_2$ represents methyl and the other represents hydrogen or methyl, or $R_1$ and $R_2$ together represent alkylene of 2 or 3 carbon atoms.

It is a further object of the invention to provide 2,2,2-trichloroethylhydroxycyclobutanones of the formula IIa or IIb

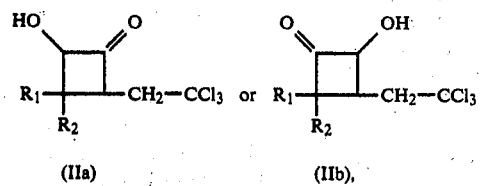

wherein $R_1$ and $R_2$ are as defined for formulae Ia and Ib. The hydroxycyclobutanones of the formulae IIa and IIb are also new.

The compounds of the formulae Ia, Ib, IIa and IIb can be obtained by converting a compound of the formula III

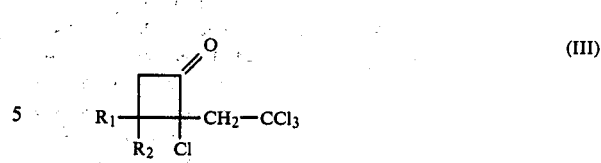

in the presence of an inorganic base, into compounds of the formulae IIa and IIb and subsequently reacting said compounds of the formulae IIa and IIb, in the presence or absence of an organic base, with a compound of the formula IV

to produce compounds of the formulae Ia and Ib. In the formulae III and IV, R, $R_1$ and $R_2$ are as defined for formulae Ia and Ib.

In the above reactions, the hydroxycyclobutanones and their sulfonic acid esters are ordinarily obtained in the form of isomer mixtures. If desired, the position isomers of the formulae IIa and IIb can be separated in a manner known per se, for example by fractional crystallisation or by chromatography. However, such a separation is not necessary for the further reaction.

An alkyl or haloalkyl group R contains advantageously 1 to 4 carbon atoms and can be straight chain or branched. Preferably, however, alkyl groups R, or alkyl moieties in haloalkyl groups R, are straight chain. Eligible haloalkyl groups R are in particular chlorinated, brominated or fluorinated alkyl groups. Examples of suitable alkyl or haloalkyl groups R are: methyl, ethyl, n-propyl, isopropyl, n-butyl, chloromethyl, trifluoromethyl and perfluoromethyl-n-butyl groups.

Possible substituents of a substituted phenyl group R are in particular alkyl groups of 1 to 4 and, in particular, 1 or 2, carbon atoms, halogen atoms, such as chlorine and bromine atoms, and nitro groups. Preferably, phenyl groups R contain only one substituent of the above kind. Examples of suitable phenyl groups R are the 3- or 4-methylphenyl, 4-ethylphenyl, 2- and 4-nitrophenyl, 4-chlorophenyl and 4-bromophenyl group.

If R is a naphthyl group, the sulfonyl group can be in the 1- or 2-position of the naphthalene radical.

Preferred compounds of the formulae Ia and Ib and of the formulae IIa and IIb are those wherein one of $R_1$ and $R_2$ is methyl and the other is hydrogen or methyl, or $R_1$ and $R_2$ together alkylene of 2 or 3 carbon atoms and R represents alkyl or haloalkyl of 1 to 4 carbon atoms, benzyl, phenyl, methylphenyl, nitrophenyl, chlorophenyl or bromophenyl.

Particularly preferred compounds of the formulae Ia, Ib, IIa and IIb are those wherein each of $R_1$ and $R_2$ represents methyl and R represents methyl, 4-methylphenyl or 4-bromophenyl.

Suitable inorganic bases for the reaction of compounds of the formula III to produce the hydroxycyclobutanones of the formulae IIa and IIb are, for example, alkali metal and alkaline earth metal hydroxides, such as sodium, potassium, calcium and barium hydroxide. Further suitable bases are carbonates and bicarbonates of alkali metals and alkaline earth metals, such as calcium, barium, potassium and sodium carbonate, sodium and potassium bicarbonate. These bases are employed in at least a stoichiometric amount; but preferably an excess is used.

The reaction is desirably carried out in an aqueous or aqueous organic medium. Suitable solvents for the reaction in aqueous organic medium are lower alcohols, for example those containing not more than 6 carbon atoms, such as methanol, ethanol, propanol, isopropanol, butanol, sec-butanol, tert-butanol, and amyl alcohols; aliphatic or cyclic ethers, such as diethyl ether, di-n-propyl ether, diisopropyl ether, tetrahydrofurane and dioxane; and aliphatic, cycloaliphatic or aromatic hydrocarbons, such as n-pentane, n-hexane, cyclohexane, benzene, toluene and xylenes.

The reaction temperatures are normally between about 20° and 100° C. and preferably between about 50° and 90° C.

When the reaction is complete, the hydroxycyclobutanones of the formulae IIa and IIb can be isolated in the usual way and, if necessary or desired, purified.

The reaction of the hydroxycyclobutanones of the formulae IIa and IIb with a compound of the formula IV in the presence of an organic base is advantageously carried out in an inert solvent. Suitable inert solvents are for example unsubstituted or chlorinated aromatic or aliphatic hydrocarbons, such as benzene, toluene, xylenes, chlorobenzene, dichlorobenzenes and trichlorobenzenes, n-pentane, n-hexane, n-octane, methylene chloride, chloroform, tetrachloromethane, 1,1,2,2-tetrachloroethane and trichloroethylene; cycloaliphatic hydrocarbons, such as cyclopentane or cyclohexane; aliphatic ketones preferably containing a total of 3 to 8 carbon atoms, such as acetone, diethyl ketone, methyl isopropyl ketone, diisopropyl ketone, methyl tert-butyl ketone; cycloaliphatic ketones, such as cyclopentanone and cyclohexanone; alkyl nitriles containing 2 to 5 carbon atoms, such as acetonitrile, propionitrile and butyronitrile; 3-alkoxypropionitriles containing 1 or 2 carbon atoms in the alkoxy moiety, such as 3-methoxypropionitrile and 3-ethoxypropionitrile; and aliphatic and cyclic ethers of the kind previously mentioned. However, the reaction can also be carried out without the addition of an inert organic solvent, for example in an excess of base.

Examples of suitable organic bases are tertiary amines, in particular trialkylamines containing 1 to 4, especially 2 to 4, carbon atoms in each of the alkyl moieties; cyclic amines, such as pyridine, quinoline, N-alkyl-pyrrolidines, N-alkyl-piperidines, N,N'-dialkyl-piperazines and N-alkyl-morpholines, or dialkyl anilines containing 1 or 2 carbon atoms in each of the alkyl moieties, such as N-methylpyrrolidine, N-ethylpiperidine, N,N'-dimethylpiperazine, N-ethylmorpholine and dimethyl aniline; and also bicyclic amidines, such as 1,5-diazabicyclo [5.4.0]-undec-5-ene and 1,5-diazabicyclo [4.3.0] non-5-ene, and bicyclic diamines, such as 1,4-diazabicyclo[2.2.2]octane.

Preferred bases are trialkylamines containing 1 to 4 carbon atoms in each of the alkyl moieties, in particular triethylamine, and pyridine. The organic base can also act simultaneously as solvent. It is employed in at least an equimolar amount to the sulfonic acid chloride of the formula IV, or else a small excess is used.

The reaction temperature is kept preferably between about −20 and +50° C., and most preferably between +10° and +30° C. The cyclobutanonesulfonates of the formulae Ia and Ib can be isolated in a manner known per se and, if necessary, purified. A separation of the resulting position isomers is in general entirely possible but not necessary for the further reaction.

The starting compounds of the formula IV can be obtained by methods which are known per se. The starting compounds of the formula III can be obtained for example by reacting carbon tetrachloride, in the presence of a catalyst and of an organic solvent, with acryloyl chloride to produce 2,4,4,4-tetrachlorobutyryl chloride, and subsequently reacting this latter, in the presence of an organic base, with a compound of the formula V

wherein $R_1$ and $R_2$ are as defined for formulae Ia and Ib, to produce a compound of the formula III.

As catalysts for the reaction of carbon tetrachloride with acryloyl chloride it is possible to use compounds which are known per se, such as metals of principal group VIII and of subgroups VIa, VIIa and Ib of the Periodic Table of the Elements (according to "Lehrbuch der anorganischen Chemie", Holleman-Wiberg, W.de Gruyter + Co., Berlin), for example iron, cobalt, nickel, ruthenium, rhodium, palladium, chromium, molybdenum, manganese and copper. These metals can be used in elementary form or in the form of compounds, such as halides or complexes with ligands. Preferred metals are iron (II) and iron (III) salts, in particular, however, copper powder, copper (I) and copper (II) salts, such as copper (I) and copper (II) chloride and copper (I) and copper (II) bromide, and mixtures thereof.

Suitable organic solvents for the above reaction are those in which the catalysts are sufficiently soluble or which are able to form complexes with the catalysts, but which are inert to the reactants. Example of such solvents are alkyl nitriles, especially those containing 2 to 5 carbon atoms, such as acetonitrile, propionitrile and butyronitrile; 3-alkoxypropionitriles containing 1 or 2 carbon atoms in the alkoxy moiety, such as 3-methoxypropionitrile and 3-ethoxypropionitrile, and aliphatic ketones containing preferably altogether 3 to 8 carbon atoms, such as acetone, diethyl ketone, methyl isopropyl ketone, diisopropyl ketone and methyl tert-butyl ketone.

The further reaction of the tetrachlorobutyryl chloride with an olefin of the formula V in the presence of a base is advantageously carried out in the presence of an inert organic solvent. Examples of such solvents are unsubstituted or chlorinated aromatic, aliphatic or cycloaliphatic hydrocarbons, aliphatic ketones, aliphatic and cyclic ethers, alkyl nitriles and 3-alkoxypropionitriles of the kind previously referred to.

As organic bases it is possible to use those of the kind already mentioned in connection with the reaction with the sulfonic acid chlorides of the formula IV, in particular trialkylamines containing 1 to 4 carbon atoms in each alkyl moiety, such as triethylamine and pyridine.

The compounds of the formulae Ia and Ib are valuable intermediates for the production of pyrethroid pesticides or precursors thereof. Compounds of this kind, for example those of the formula VI

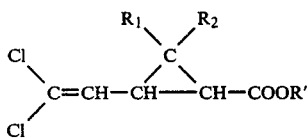 (VI), wherein
$R_1$ and $R_2$ are as defined for formulae Ia and Ib,
$R'$ represents hydrogen, alkyl of 1 to 4 carbon atoms or a group of the formula

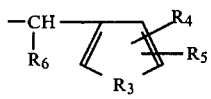

in which $R_3$ represents —O—, —S— or —CH=CH—,
$R_4$ represents hydrogen, alkyl of 1 to 4 carbon atoms, benzyl, phenoxy or phenylmercapto, $R_5$ represents hydrogen or alkyl of 1 to 4 carbon atoms and $R_6$ represents hydrogen or ethynyl, or, if one of $R_1$ and $R_2$ represents methyl and the other represents hydrogen or methyl, $R_3$ represents —CH=CH—, $R_4$ represents phenoxy and $R_5$ represents hydrogen, $R_6$ also represents alkyl or 1 to 5 carbon atoms, can be obtained by converting a compound of the formulae Ia or Ib or mixtures thereof, in the presence of a base, for example a compound of the formula VII $$M^{n+} (O^-R')_n \quad (VII),$$

wherein M is an alkali metal cation or an alkaline earth metal cation and n is 1 or 2 and $R'$ is as defined for formula VI, into a compound of the formula VI.

The compounds of the formula VI can be obtained in the form of cis- or trans-isomers (with respect to the —COOR' and the dichlorovinyl group) or as mixtures of cis- and trans- isomers.

As bases of the formula VII it is possible to use, for example, sodium, potassium, calcium and barium hydroxide, or sodium and potassium methylate, ethylate, isopropylate, sec-butylate or tert-butylate, magnesium methylate or sodium and potassium salts of benzyl alcohol, m-phenoxybenzyl alcohol, furfuryl alcohol or 2-thiophenemethanol.

Suitable bases are also carbonates and bicarbonates of alkali metals and alkaline earth metals, such as calcium, barium, potassium and sodium carbonate, sodium and potassium bicarbonate. At least a stoichiometric amount, but preferably an excess, of base is used.

Depending on the nature of the base, the reaction is carried out advantageously in an aqueous-organic or organic medium. If an alkali metal carbonate or alkaline earth metal carbonate is used as base, the reaction is carried out in an aqueous or aqueous-organic medium. The reaction in the presence of an alkali metal hydroxide or alkaline earth metal hydroxide and an alkali metal bicarbonate is also carried out with advantage in an aqueous or aqueous-organic medium.

Suitable organic solvents for the reaction in aqueous organic or organic medium are lower alcohols for example those containing not more than 6 carbon atoms, such as methanol, ethanol, propanol, isopropanol, butanol, sec -butanol, tert -butanol and amyl alcohols, aliphatic or cyclic ethers, such as diethyl ether, di-n-propyl ether, diisopropyl ether, tetrahydrofurane and dioxane, and aliphatic, cycloaliphatic or aromatic hydrocarbons, such as n-pentane, n-hexane, cyclohexane, benzene, toluene and xylenes.

Compounds of the formula VI, in which $R'$ is hydrogen or alkyl, can be converted in a manner which is known per se into compounds of the formula VI wherein $R'$ is a group of the formula

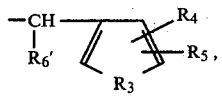

wherein $R_3$, $R_4$ and $R_5$ are as defined for formula VI and $R_6'$ has the same meaning as $R_6$ or represents a —CN— group, for example by reaction with corresponding halides or alcohols (in the latter case while optionally converting the compound of the formula VI beforehand into the acid chloride) or by transesterification.

Compound of the formula VIII

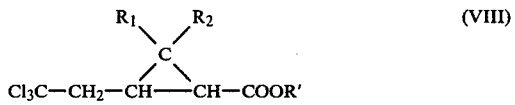 (VIII)

are obtained as intermediates when converting compounds of the formulae Ia and Ib into compounds of the formula VI. The compounds of the formula VIII can be isolated in simple manner by keeping the reaction temperature below about 40° C. and/or adding a less than equivalent amount of base. Above this temperature, or with the addition of further base, the compounds of the formula VIII are converted into compounds of the formula VI by dehydrochlorination. Compounds of the formula VI, in which $R'$ is not hydrogen or alkyl of 1 to 4 carbon atoms, are suitable for controlling a variety of animal and plant pests, especially in the form of insecticides. Compounds of the formula VI in which $R'$ is hydrogen or alkyl of 1 to 4 carbon atoms, can be converted into such active substances in a manner known per se. The properties, fields of use and formulations of these active substances are described in the literature [cf. for example Nature, 246, 169–70 (1973); Nature, 248,710–11(1974); Proceedings 7th Brithish Insecticide and Fungicide Conference, 721–728 (1973); Proceedings 8th British Insecticide and Fungicide Conference, 373–78 (1975); J.Agr.Food Chem., 23,115 (1973); U.S. Pat. No. 3,961,070; German Offenlegungsschriften Nos. 2,553,991, 2,439,177, 2,326,077 and 2,614,648; ACS Symp. Ser. 42,1 (1977)].

The novel intermediates of the formulae Ia, Ib, IIa and IIb make it possible to obtain compounds of the formula VI in a particularly easy and economic manner, in good to very good yield, and with a high content of the cis-form which is especially effective in specific end-uses and therefore desired. In contrast to known methods of obtaining compounds of the formula VI [cf. for example Farkas et al., Coll.Czech.Chem. Comm., 24, 2230 (1959) and Chem. Listy, 52, 688 (1959); British Patent No. 1.285.350; Belgian Patent No. 850.402, German Offenlegungsschriften Nos. 2.417.615, 2.439.177, 2.539.048, 2.539.895, 2.544.150, 2.547.510, 2.552.615, 2.554.380, 2.605.398, 2.615.159, 2.615.160, 2.616.528, 2.621.830, 2.621,832, 2.621.833, 2.621,835, 2.623.777, 2.630,981, 2.638.356 and 2.639.777, 2.654.060, 2.654.061, 2.654.062, U.S. Pat. Nos. 3,961,070, 4,096,170 and Japanese published patent specifications Nos. 69872/76 and 47966/76], the starting materials are easy to prepare, the reactants are comparatively cheap and ecologically safe, all reaction steps can be carried out under relatively mild conditions and without complicated apparatus and safely measures. The starting compounds of the formula III and the compounds of the formulae Ia, Ib, IIa and IIb have the degree of oxidation necessary for the further use, so that neither oxidation nor reduction steps are necessary. The individual process steps can also be carried out directly without isolating the respective intermediate, so that the synthesis is highly suitable for the large-scale production of compounds of the formula VI via the compounds of the formulae Ia, Ib, IIa and IIb.

The invention is illustrated by the following Examples.

EXAMPLE 1

(a) Manufacture of 2,4,4,4-tetrachlorobutyryl chloride 452.5 g (5 moles) of acryloyl chloride (of technical purity), 1.5 liters of carbon tetrachloride, 1.5 liters of acetonitrile and 30 g of copper (I) chloride are kept for 24 hours at 115° C. The reaction mixture is filtered clear and evaporated in a water jet vacuum. The residue is distilled, affording 922 g (76% of theory) of the title compound with a boiling point of 78°–80° C./11 mm Hg.

IR spectrum (CHCl$_3$) in cm $^{-1}$: 1780 (C=O).

NMR spectrum (100 MHz, CDCl$_3$) in ppm: 3.16–3.94 (m), 2H (CH$_2$); 4.84–4.96 (m), 1H (CH).

(b) Manufacture of 2-chloro-2-(2',2',2'-trichlorethyl)-3,3-dimethylcyclobutan-1-one In an autoclave, 280 g of isobutylene are added under pressure to 122 g (0.5 mole) of 2,4,4,4-tetrachlorobutyryl chloride in 600 ml of cyclohexane. A solution of 51 g (0.5 mole) of triethylamine in 500 ml of cyclohexane is then pumped in at 65° C. The reaction mixture is then kept for 3 hours at 65° C. The precipitated hydrochloride of triethylamine is collected by filtration and the filtrate is concentrated. The resulting crystals are collected by filtration, affording 79.4 g of 2-chloro-2-(2',2',2'-trichloroethyl)-3,3-dimethylcyclobutan-1-one with a melting point of 75°–76° C. (60% of theory).

IR spectrum (CHCl$_3$) in cm $^{-1}$: 1805 (C=O).

$^1$H-NMR spectrum (100 MHz, CDCl$_3$) in ppm: 1.42 and 1.45 (s), 6H each (1 CH$_3$); 2.91–3.28 (m), 2H (CH$_2$); 3.37–3.76 (m), 2H(CH$_2$).

$^{13}$C-NMR spectrum (CDCl$_3$) in ppm: 196 (s), (CO); 95.3 (s), (CH$_3$); 80.8 (s), (C-2); 57.0 (t,CH$_2$); 56.4 (t, CH$_2$); 37.9 (s), (C-3); 25.1 (q, CH$_3$); 28.8 (q, CH$_3$).

Elemental analysis for C$_8$H$_{10}$Cl$_4$O (mol.wt. 263.98): calculated: C, 36.40%; H,3.82%; O,6.02%; Cl,53.72%. found: C,36.4%; H,3.9%; O,6.2%; Cl,53.5%.

(c) Manufacture of 2-(2',2',2'-trichloroethyl)-3,3-dimethyl-4-hydroxycyclobutanone (A) and 2-hydroxy-3-(2',2',2'-trichloroethyl)-4,4-dimethylcyclobutanone (B)

52.8 g (0.2 mole) of 2-chloro-2-(2',2',2'-trichloroethyl)-3,3-dimethylcyclobutanone, 500 ml of 1N Na$_2$CO$_3$ solution and 20 ml of dioxane are stirred for 6 hours at 70° C. The reaction mixture is then acidified with semi-concentrated hydrochloric acid and extracted with diethyl ether. The extract is washed with water, dried over magnesium sulfate and concentrated, yielding a viscous oil which consists of a mixture of both compounds A and B. IR spectrum (CHCl$_3$) in cm$^{-1}$:3300 (OH), 1780 (C=O).

NMR spectrum (CDCl$_3$/D$_2$O) in ppm:
Compound (A) 4.71 (d, J=2Hz, 1H (H at C-4); 2.6–3.3 (m), 3H (—CH—CH$_2$—); 1.00 and 1.60 (s), 3H(CH$_3$ each).
Compound (B): 4.90 (d, J=8 Hz), 1H (H at C-2); 2.65–3.3 (m), 3H(—CH—CH$_2$—); 1.23 and 1.41 (s), 3H (CH$_3$ each).

EXAMPLE 2

2-(2',2',2'-Trichloroethyl)-3,3-dimethyl-4-(p-tolyl)-sulfonyloxycyclobutanone (C) and 2-(p-tolyl)-sulfonyloxy-3-(2',2',2'-trichloroethyl)-4,4-dimethylcyclobutanone (D)

24.55 g (0.1 mole) of the mixture of compounds A and B obtained in Example 1(c) are dissolved in 120 ml of absolute pyridine. Then 19 g (0.1 mole) of toluene-4-sulfochloride are stirred in at room temperature (20°–25° C.) in portions. Stirring is continued for 4 hours and the reaction solution is then poured on ice and extracted with diethyl ether. The extract is washed with water, dilute hydrochloric acid and finally again with water, dried over magnesium sulfate and concentrated. The residue is crystallised from diethyl ether/n-hexane, affording the compounds C and D in the ratio of 2:1. Melting point: 78°–79° C.

IR spectrum (CHCl$_3$) in cm$^{-1}$: 1805 (C=O), 1374, 1193 and 1180 (—O—SO$_2$—).

NMR spectrum (CDCl$_3$) in ppm:
Compound (C): 7.6 (AB, J=8 Hz), 4H (aromat.); 5.20 (d, J=2 Hz), 1H (H at C-4); 2.6–3.3 (m), 3H(CH—CH$_2$); 2.47 (s), 3H(CH$_3$); 1.08 and 1.57 (s), 3H(CH$_3$ each).
Compound (D): 7.6 (AB, J=8 Hz), 4H (aromat.); 5.38 (d, J=8 Hz), 1H(H at C-2); 2.6–3.3(m), 3H(CH—CH$_2$); 2.47(s), 3H(CH$_3$); 1.23 and 1.32 (s), 3H(CH$_3$ each).

EXAMPLE 3

2-(2',2',2'-Trichloroethyl)-3,3-dimethyl-4-(p-bromophenyl)-sulfonyloxycyclobutanone (E) and 2-(p-bromophenyl)-sulfonyloxy-3-(2',2',2'-trichloroethyl)-4,4-dimethylcyclobutanone (F)

9.8 g (40 mmols) of the oil obtained in Example 1 (c) are dissolved in 50 ml of anhydrous pyridine. Then 10.2 g (40 mmols) of bromophenyl-4-sulfochloride are added at room temperature and the reaction mixture is stirred for 5 hours. The reaction products are worked up as described in Example 2. Recrystallisation from diethyl ether yields a mixture of compounds E and F.

IR spectrum (CHCl$_3$) in cm $^{-1}$: 1800 (C=O); 1375, 1195 and 1180 (—O—SO$_2$—).

NMR spectrum (CDCl$_3$) in ppm:
Compound (E): 7.76 (AB), 4H (aromat.); 5.23 (d, J=2 Hz), 1H(H at C-4); 2.65–3.47 (ABX), 3H(CH—CH$_2$); 1.10 and 1.61 (s) 3H(CH$_3$ each).
Compound (F): 7.65 (AB), 4H(aromat.); 5.44 d, J=8 Hz), 1H(H at C-2); 3.14 (d, J=6 Hz), 2H(CH$_2$); 2.65–2.85 (m), 1H (H at C-3); 1.25 and 1.34 (s), 3H(CH$_3$ each).

The two position isomers E and F can be separated by fractional crystallisation from diethyl ether or by chromatography on silica gel with toluene/ethyl acetate (in the volume ratio of 4:1) as eluant. Melting point of compound E: 112° C.; melting point of compound F: 150° C. (both crystallised from diethyl ether).

EXAMPLE 4

2-(2',2',2'-Trichloroethyl)-3,3-dimethyl-4-methylsulfonyloxycyclobutanone (G) and 2-methylsulfonyloxy-3-(2',2',2'-trichloroethyl)-4,4dimethylcyclobutanone (H)

11.1 g (45.2 mmols) of the oil obtained in Example 1 (c) are dissolved in 60 ml of anhydrous pyridine. To this solution are added 5.05 g (45.2 mmols) of methanesulfonyl chloride such that the temperature of the reaction mixture does not exceed 25° C. The reaction mixture is stirred for 3 hours at room temperature, then poured on ice and worked up as described in Example 2. The two position isomers G and H are obtained in the form of a viscous oil.

IR spectrum (CDCl₃) in ppm: Compound (G): 5.34 (d, J=2 Hz), 1H (H at C-4); 2.7-3.4 (ABX), 3H (—CH₂—CH—); 3.18 (s), 3H (—O—SO₂—CH₃); 1.13 and 1.66 (s), 3H(CH₃ each).

Compound (H): 5.50 (d, J=8 Hz), 1H (H at C-2); 3.20 (s), 1H(—O—SO₂CH₃); 2.7-3.4 (m), 3H(—CH₂—CH—); 1.39 and 1.28 (s), 3H(CH₃ each).

EXAMPLE 5

8.6 g (34 mmols) of the oil obtained in Example 1 (c) are dissolved in 50 ml of absolute carbon tetrachloride, and to this solution are added 3.9 g (34 mmols) of methanesulfonyl chloride. With cooling (10° C.), 3.5 g (34 mmols) of triethylamine in 10 ml of carbon tetrachloride are added dropwise and the mixture is stirred for 30 minutes. The precipitated triethylamine hydrochloride is collected by filtration and the filtrate is concentrated. The two isomers (G) and (H) are obtained in the form of a viscous oil. The spectroscopic data of these isomers are identical with those of the compounds obtained in Example 4.

EXAMPLE 6

3.7 g (36 mmols) of triethylamine in 10 ml of carbon tetrachloride are added dropwise to 9.36 g (36 mmols) of bromophenyl-4-sulfochloride and 9 g (36 mmols) of the oil obtained in Example 1(c) in 70 ml of carbon tetrachloride such that the temperature of the reaction mixture does not exceed 30° C. The mixture is stirred for 2 hours and the precipitated triethylamine hydrochloride is collected filtration and the filtrate is concentrated. The solid residue is recrystalised from diethyl ether, affording the compounds (E) and (F), the physical data of which are identical with those of the compounds obtained in Example 3.

EXAMPLE 7

(a) 2 g (5 mmols) of the mixture of compounds (C) and (D) obtained in Example 2 are stirred with 35 ml of 2N sodium hydroxide and 1 ml of dioxane for 6 hours at room temperature. The clear reaction solution is washed with diethyl ether, acidified with semiconcentrated hydrochloric acid and extracted with diethyl ether. The extract is washed with water, dried over magnesium sulfate and concentrated. Crystallisation from diethyl ether yields 1.1 g (89% of theory) of 2-(2',2',2'-trichloroethyl)-3,3-dimethylcyclopropanecarboxylic acid with a melting point of 85°-89° C.

(b) The procedure of (a) is repeated, except that the reaction mixture is stirred for 6 hours at room temperature and subsequently heated for 3 hours to 90° C. Working up in the known manner yields 2-(2',2'-dichlorovinyl)-3,3-dimethylcyclopropanecarboxylic acid with a melting point of 81°-85° C.

(c) 2.35 g (5 mmols) of the isomer (E) obtained in Example 3 are stirred in 20 ml of 10% sodium hydroxide at room temperature. After 2 hours, the mixture is diluted with 30 ml of water and again stirred for 2 hours at room temperature. The now clear solution is worked up in the conventional manner, yielding 0.69 g (94% of theory) of pure cis-2-(2',2',2'-trichloroethyl)-3,3-dimethylcyclopropanecarboxylic acid with a melting point of 92° C.

¹³C-NMR spectrum (CDCl₃) in ppm: 178.4 (COOH); 99.8 (CCl₃); 49.2 (CH₂), 30.6 and 28.7 (C-1, C-3); 26.5 (C-2): 28.6 (CH₃ trans with respect to CO); 14.7 (CH₃ cis with respect to CO).

(d) 4.7 g (10 mmols) of the isomer (E) obtained in Example 3 are stirred in 50 ml of 10% sodium hydroxide at 0° C. After 2 hours, the reaction mixture is kept for 4 hours at 90° C. and then worked up in the usual manner, affording 1.6 g(90% of theory) of pure cis-2-(2', 2'-dichlorovinyl)-3,3-dimethylcyclopropanecarboxylic acid with a melting point of 86° C.

NMR spectrum (CDCl₃/D₂O) in ppm: 6.17 (d, J=8.5 Hz), 1H (—C$\underline{H}$=CCl₂); 2.02-2.2 (m), 1H (H on C-3); 1.85 (d, J=9 Hz), 1H (H on C-1); 1.30 (s), 6H (2 CH₃).

(e) The mixture of compounds (G) and (H) obtained in Example 4 is converted onto 2-(2',2',2'-trichloroethyl)-3,3-dimethylcyclopropanecarboxylic acid as described in (a) and (c). According to the NMR spectrum, the cis/trans ratio is 7:3.

(f) The mixture of compounds (G) and (H) obtained in Example 4 is converted into 2-(2',2'-dichlorovinyl)-3,3-dimethylcyclopropanecarboxylic acid as described in (b) and (d). The cis/trans ratio determined by NMR spectroscopy is 4:1.

(g) The isomer (f) obtained in Example 3 is reacted with sodium hydroxide solution as in (d), yielding 2-(2',2'-dichlorovinyl)-3,3-dimethylcyclopropanecarboxylic acid with a cis/trans ratio of 2:1 (determined by NMR spectroscopy).

MANUFACTURE OF INSECTICIDAL ACTIVE INGREDIENTS (a) 4.18 g (0.02 mole) of 2-(2',2'-dichlorovinyl-3,3-dimethylcyclopropane-1-carboxylic acid and 20 ml of thionyl chloride are heated for 3 hours to 70° C. Excess thionyl chloride is then evaporated off. The residue is taken up in 100 ml of benzene and the solution is concentrated. The residue, consisting of 2-(2',2'-dichlorovinyl)-3,3-dimethylcyclopropanecarboxylic acid chloride, is treated with a solution of 4 g (0.02 mole) of m-phenoxybenzyl alcohol in 40 ml of absolute benzene and the mixture is warmed to 40° C. Then 2.2 g (0.022 mole) of triethylamine in 10 ml of absolute benzene are added dropwise in the course of one hour and the reaction mixture is washed with dilute hydrochloric acid, dried over magnesium sulfate and concentrated. The residue is chromatographed over silica gel with diethyl ether /n-hexane as eluant (volume ratio of 1:4), affording the m-phenoxybenzyl ester of 2-(2',2'-dichlorovinyl)-3,3-dimethylcyclopropane-1-carboxylic acid with a refractive index of $n_D^{20}$=1.5628.

(b) 10 g (0.047 mole) of cis-2-(2',2'-dichlorovinyl)-3,3-dimethylcyclopropanecarboxylic acid are stirred in 100 ml of benzene with 12.1 ml (0.141 mole) of oxalyl chloride for 24 hours at room temperature. The reaction solution is evaporated and the brown residue is distilled under reduced pressure, affording 9.1 g of a clear liquid with a boiling point of 50° C./0.04 mm Hg. 3 g of this clear liquid are then dissolved in 30 ml of toluene and 2 ml of pyridine are added to the solution. Then 2.9 g of α-cyano-m-phenoxybenzyl alcohol in 20 ml of toluene are added dropwise at room temperature and the reaction mixture is subsequently stirred for 16 hours at room temperture. The reaction mixture is washed firstly with water, then with saturated sodium bicarbonate solution and finally with saline solution, dried over magnesium sulfate and concentrated. The residue is chromatographed over silica gel (elution wth diethyl ether /n-hexane in the ratio 1:2). affording pure α-cyano-m-phenoxybenzyl cis-2-(2',2'-dichlorovinyl)-3,3-dimethyl-cyclopropanecarboxylate in the form of a diastereoisomer mixture. NMR spectrum (60 MHz, CDCl$_3$) in ppm: 1.20–1.43 (m), 6H(2CH$_3$); 1.67–2.35 (m), 2H(2 CH); 6.25 (d, J=9 Hz), 1H(CH=CCl$_2$); 6.40 and 6.45 (s), 0.5H each (C$\underline{H}$—CN); 6.98–7.65 (m), 9H.

What is claimed is:

1. A compound of the formula

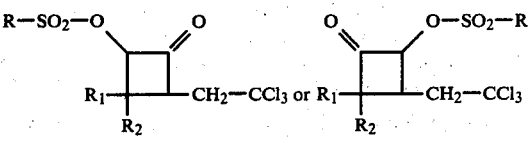

wherein
R represents alkyl or haloalkyl of 1 to 4 carbon atoms, benzyl, phenyl, methylphenyl, nitrophenyl, chlorophenyl or bromophenyl, and
one of R$_1$ and R$_2$ represents methyl and the other represents hydrogen or methyl or R$_1$ and R$_2$ together represent alkylene of 2 or 3 carbon atoms.

2. A compound according to claim 1, wherein R represents methyl, 4-methylphenyl or 4-bromophenyl, one of R$_1$ and R$_2$ represents methyl and the other of R$_1$ and R$_2$ represents hydrogen or methyl.

* * * * *